(12) United States Patent
Vivekananda et al.

(10) Patent No.: US 9,217,134 B1
(45) Date of Patent: Dec. 22, 2015

(54) **APTAMER DRUG FOR DETOXIFICATION OF *STAPHYLOCOCCUS AUREUS* ALPHA-TOXIN**

(71) Applicants: Jeevalatha Vivekananda, San Antonio, TX (US); Nancy J. Millenbaugh, San Antonio, TX (US)

(72) Inventors: Jeevalatha Vivekananda, San Antonio, TX (US); Nancy J. Millenbaugh, San Antonio, TX (US)

(73) Assignee: The United States of America as Represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 14/470,506

(22) Filed: Aug. 27, 2014

(51) Int. Cl.
*C12N 15/115* (2010.01)
*C12Q 1/68* (2006.01)
*C12N 1/20* (2006.01)
*G01N 33/50* (2006.01)

(52) U.S. Cl.
CPC .............. *C12N 1/20* (2013.01); *G01N 33/5091* (2013.01)

(58) Field of Classification Search
None
See application file for complete search history.

(56) References Cited

PUBLICATIONS

Thomsen et al (BMC Bioinformatics 2007, 8(Suppl 7):S11)).*
Cao et al (Nucleic Acids Research, 2009, vol. 37, No. 14 4621-4628).*

* cited by examiner

*Primary Examiner* — Richard Schnizer
(74) *Attorney, Agent, or Firm* — Ning Yang; Albert M. Churillo; Diane P. Tso (57) ABSTRACT

Aptamers and methods of use thereof are presented for the treatment or diagnosis of *Staphylococcus aureus* infection. The aptamers binds to and capable of neutralization of *Staphylococcus aureus* alpha-toxin.

5 Claims, 6 Drawing Sheets

APTAMER DRUG FOR DETOXIFICATION OF *STAPHYLOCOCCUS AUREUS* ALPHA-TOXIN

CROSS-REFERENCES OF RELATED APPLICATIONS

This application claims priority to Provisional Application No. 61/870,263, filed Aug. 27, 2013, the entire text of which is hereby incorporated by reference.

FIELD OF THE INVENTION

The present invention provides aptamer targeting alpha toxin and methods for using these aptamers for the detoxification of bacterial toxin, specifically *Staphylococcus aureus* alpha-toxin.

BACKGROUND

Infectious complications of trauma injuries often require treatment of multi-drug resistant bacterial pathogens, and their secreted toxins. Bacterial toxins play a significant role in pathogenesis, virulence, tissue damage and inflammation. War wound infections have long posed a major challenge for military medicine and, infectious complications will remain a major cause of morbidity and mortality.

US casualties from Iraq and Afghanistan often have wounds that are colonized or infected with multidrug-resistant strains of *Staphylococcus aureus*. Other frequently identified resistant strains of bacteria are *Klebsiella pneumoniae, Pseudomonas aeruginosa* and *Acinetobacter baumannii*. Overuse of broad-spectrum antibiotics may be the primary cause in emergence of these resistant strains [1]. In addition, these pathogens secrete toxins which enhance virulence and tissue damage. Such factors likely lead to hard to heal wounds.

When toxin producing pathogens invade and multiply in tissues, it is likely that during infection, sensitive cells will be exposed to their products, such as toxins that provoke active cellular responses. Synthesis and secretion of inflammatory cytokines is, of course, one of the countless possible reactions that will follow as a consequence of infections. *S. aureus* expresses numerous virulence factors including α-toxin/hemolysin that are aimed at weakening the immune system by direct inactivation of key innate response molecules. As a pore forming factor, α-toxin plays a major role in the pathogenesis of *S. aureus* infections and, therefore, is an important target for therapeutic intervention [8, 11]. Although early intervention with antibiotics can reduce the bacterial burden, inhibitors of secreted toxins could offer a therapeutic advantage in the later stages of infection involving toxemia. Currently, no such inhibitors are available to neutralize α-toxin mediated cytolytic and cytotoxic effects. Therefore, the present invention was undertaken to identify DNA based inhibitors/aptamers to detoxify α-toxin induced toxicity in *S. aureus* infections.

Aptamers represent a class of macromolecules with attractive drug properties which could be useful in the treatment of a variety of ailments. Aptamers are nucleic acids having specific binding affinity to multiple types of molecules through interactions other than classic Watson-Crick base pairing. Aptamers, like peptides generated by phage display or monoclonal antibodies ("MAbs"), are capable of specifically binding to selected targets, and modulating the target's activity. For example, binding of aptamers to a target may block the target's ability to function. Created by an in vitro selection process from pools of random sequence oligonucleotides, aptamers have been generated for over 100 proteins including growth factors, transcription factors, enzymes, immunoglobulins, and receptors. A typical aptamer is 10-15 kDa in size, consists of 30-45 nucleotides, binds its target with sub-nanomolar affinity, and discriminates against closely related targets. Aptamers will typically not bind other proteins from the same gene family. A series of structural studies have shown that aptamers are capable of using the same types of binding interactions, such as hydrogen bonding, electrostatic complementarity, hydrophobic contacts and steric exclusion that drive affinity and specificity in antibody-antigen complexes.

Aptamers have a number of desirable characteristics for use as therapeutics and diagnostics including high specificity and affinity, biological efficacy, and excellent pharmacokinetic properties. In addition, they offer specific competitive advantages over antibodies and other protein biologics, for example speed and control. Aptamers are produced by an entirely in vitro process, allowing for the rapid generation of initial leads, including therapeutic leads. In vitro selection allows the specificity and affinity of the aptamer to be tightly controlled, and allows the generation of leads, including leads against both toxic and non-immunogenic targets.

Aptamers as a class have demonstrated little or no toxicity or immunogenicity. In chronic dosing of rats or woodchucks with high levels of aptamer (10 mg/kg daily for 90 days), no toxicity is observed by any clinical, cellular, or biochemical measure. Whereas the efficacy of many monoclonal antibodies can be severely limited by immune response to antibodies themselves, it is extremely difficult to elicit antibodies to aptamers most likely because aptamers cannot be presented by T-cells via the MHC and the immune response is generally trained not to recognize nucleic acid fragments.

Aptamers (protein-binding oligonucleotides) have great potential as a new class of targeted therapeutics. These molecules are artificial, single-stranded nucleic acid ligands (DNA and RNA) generated against amino acids, proteins, drugs, viruses and whole cells [2]. They are discovered by an in vitro directed evolution process called SELEX but are ultimately chemically synthesized like small molecule therapeutics using solid-phase techniques that are easily scaled up and allow for modification and conjugation strategies [3, 4, and 5]. Aptamers emerged as a new class of molecules that rival antibodies in both therapeutic and diagnostic applications. One of the advantages of DNA-based aptamer drugs over currently available low molecular weight pharmaceuticals or antibodies is their selective recognition of molecular targets which imparts tremendous specificity of action with binding affinities in the low nano- to picomolar range. Because of their unique three dimensional structures, aptamers are able to bind to functional domains of the target, thereby modulating the biological function of the molecule. Their small size enables them to access epitopes that might otherwise be blocked or hidden. Aptamer selection and identification is much faster than monoclonal antibodies and allows optimization of binding affinity by successive rounds of selection and screening. Antibodies generally elicit strong immune responses due to their size, whereas aptamers show little or no immunogenicity. Further, aptamers are thermally stable and preserve their structure over a wide range of temperatures, exhibit low toxicity, and can be generated to recognize a wide range of targets, including small molecules and ions.

In spite of the infancy of aptamer therapeutics, these molecules have produced striking results in both preclinical and clinical studies. Several aptamers are currently in clinical trials, or being evaluated, for different diseases [25, 26]. To date, there are a few aptamers identified against bacterial and plant toxins that have the potential to inhibit the biological functions of the respective toxin both in vitro and in vivo [27-29]. Recent work by Liang et al. further reinforces the therapeutic potential of aptamers targeting rabies virus and demonstrated the aptamer mediated inhibition of rabies viral multiplication both in vitro and in vivo [30]. Most notably, the only DNA aptamer identified against one of the *S. aureus* exoproteins was against enterotoxin B (SEB) and is designated as APTSEB. This aptamer was developed not as a therapeutic, but to be used in the diagnostic platform to detect SEB [31].

The present invention provides novel small drug molecules or aptamers and method of using them to neutralize the lethal effects of *Staphylococcus aureus* alpha toxin for treatment of *S. aureus* infections.

DESCRIPTION OF FIGURES

FIG. 4A. Cytokine gene expression elicited by α-toxin (AT) and their inhibition by α-toxin aptamers. Jurkat T cells were stimulated either with (A) α-toxin at 50 ng/ml alone or in combination with AT-36 aptamer at 500× or 1000× molar excess of α-toxin for 6 hours (TNF-α). Cells grown in media without toxin served as control (CTRL). Total cellular RNA extracted from the Jurkat T cells was analyzed for TNF-α and IL-17 expression using RT-PCR. The PCR products were run on 2% agarose gels and stained with ethidium bromide. Gels were imaged with an AlphaImager HP System (Protein Simple). TNF-α and IL-17 gene expression was normalized to GAPDH, n=3.

FIG. 4B Cytokine gene expression elicited by α-toxin (AT) and their inhibition by α-toxin aptamers. Jurkat T cells were stimulated either with α-toxin at 100 ng/ml alone or in combination with AT-33 or AT-36 at 500× molar excess of α-toxin for 24 hours (IL-17). Cells grown in media without toxin served as control (CTRL). Total cellular RNA extracted from the Jurkat T cells was analyzed for TNF-α and IL-17 expression using RT-PCR. The PCR products were run on 2% agarose gels and stained with ethidium bromide. Gels were imaged with an AlphaImager HP System (Protein Simple). TNF-α and IL-17 gene expression was normalized to GAPDH, n=3.

DESCRIPTION OF THE INVENTION

The details of one or more embodiments of the invention are set forth in the accompanying description below. Although any methods and materials similar or equivalent to those described herein can be used in the practice or testing of the present invention, the preferred methods and materials are now described. Other features, objects, and advantages of the invention will be apparent from the description. All references cited herein are incorporated in its entirety.

Definition

In the present specification, by the "in vitro selection method" is meant a method for obtaining a nucleic acid molecule having a particular function by repeatedly performing a selection process including separation of a single strand oligonucleotide having a particular function (e.g., specific adsorption to a target substance) from a randomly synthesized single strand oligonucleotide library, amplification of the oligonucleotide, and separation of a single strand oligonucleotide having the above-mentioned particular function. When a nucleic acid molecule (aptamer) capable of specific adsorption to a particular target substance is to be obtained from a random oligonucleotide library, the above-mentioned nucleic acid molecule capable of adsorption is separated by, for example, affinity chromatography using an affinity column having a target substance immobilized thereon.

In the present specification, by the "aptamer" is meant a single strand nucleic acid molecule capable of specific adsorption to a particular target substance. The aptamer in the present specification is not limited to those obtained by the above-mentioned in vitro selection method.

In the present application, by the "neutralization/inhibition" is meant neutralization or inhibition of toxin, such as blocking the pore-forming and cytotoxic activity of alpha-toxin, which leads to increased cell viability.

The SELEX™ Method

In the present specification, by the "affinity chromatography" is meant a separation method utilizing a specific interaction (affinity) that a biological substance shows. The separation means is not particularly limited, and various methods usually employed in the pertinent field are used. To be specific, affinity chromatography using an affinity column is exemplified. This method includes at least the steps of (i) applying a substance capable of specifically adsorbing to a target substance and/or a substance incapable of adsorbing to an affinity column packed with a carrier having a target substance immobilized thereon (hereinafter sometimes to be conveniently referred to as a target substance-immobilized affinity column), (ii) washing, after the application, the column with a washing buffer to separate the above-mentioned substance capable of adsorption from a substance incapable of adsorption (washing treatment), and (iii) weakening, after the washing treatment, the bonding force between a substance capable of adsorption and the target substance immobilized on the column, with an elution buffer to allow elution of the substance capable of adsorption (elution treatment). As the carrier used for immobilizing the target substance, those known to be used for affinity chromatography, particularly affinity column chromatography, are mentioned.

SELEX™ stands for "Systematic Evolution of Ligands by Exponential Enrichment" ("SELEX™"), which is first described in 1990 by Szostak. The SELEX™ process was modified over the years in different ways to become more efficient and less time consuming to reach higher affinities of the aptamers selected for automation of the process, which are explained in review article by Stoltenburg [33]. The SELEX™ process is a method for the in vitro evolution of nucleic acid molecules with highly specific binding to target molecules, and its usage is taught in abandoned, U.S. Pat. No. 5,475,096 entitled "Nucleic Acid Ligands", and U.S. Pat. No. 5,270,163 (see also WO 91/19813) entitled "Nucleic Acid Ligands". Each SELEX-identified nucleic acid ligand is a specific ligand of a given target compound or molecule. In the present application, SELEX™ is used to select aptamers for neutralization of *Staphylococcus aureus* alpha toxin.

The SELEX™ process is based on the concept that nucleic acids have sufficient capacity for forming a variety of two- and three-dimensional structures, and sufficient chemical versatility available within their monomers to act as ligands (form specific binding pairs) with virtually any chemical compound, whether monomeric or polymeric. Molecules of any size or composition can serve as targets.

SELEX™ relies as a starting point upon a large library of single stranded oligonucleotide (RNA or ssDNA) templates comprising randomized sequences derived from chemical synthesis on a standard DNA synthesizer. In some examples, a population of 100% random oligonucleotides is screened. In others, each oligonucleotide in the population comprises a random sequence, and at least one fixed sequence at its 5' and/or 3' end which comprises a sequence shared by all the molecules of the oligonucleotide population. Fixed sequences include sequences such as hybridization sites for PCR primers, promoter sequences for RNA polymerases (e.g., T3, T4, T7, SP6, and the like), restriction sites, or homopolymeric sequences, such as poly A or poly T tracts, catalytic cores (described further below), sites for selective binding to affinity columns, and other sequences to facilitate cloning and/or sequencing of an oligonucleotide of interest.

The random sequence portion of the oligonucleotide can be of any length and can comprise ribonucleotides and/or deoxyribonucleotides and can include modified or non-natural nucleotides or nucleotide analogs as described, e.g., in U.S. Pat. Nos. 5,958,691; 5,660,985; 5,958,691; 5,698,687; 5,817,635; 8,318,438 and 5,672,695, PCT publication WO 92/07065. Random oligonucleotides can be synthesized from phosphodiester-linked nucleotides using solid phase oligonucleotide synthesis techniques well known in the art (Froehler et al., Nucl. Acid Res. 14:5399-5467 (1986); Froehler et al., Tet. Lett. 27:5575-5578 (1986)). Oligonucleotides can also be synthesized using solution phase methods such as triester synthesis methods (Sood et al., Nucl. Acid Res. 4:2557 (1977); Hirose et al., Tet. Lett., 28:2449 (1978)). Typical syntheses carried out on automated DNA synthesis equipment yield $10^{15}$-$10^{17}$ molecules. Sufficiently large regions of random sequence in the sequence design increases the likelihood that each synthesized molecule is likely to represent a unique sequence.

To synthesize randomized sequences, mixtures of all four nucleotides are added at each nucleotide addition step during the synthesis process, allowing for random incorporation of nucleotides. In one embodiment, random oligonucleotides comprise entirely random sequences. However, in other embodiments, random oligonucleotides can comprise stretches of nonrandom or partially random sequences. Partially random sequences can be created by adding the four nucleotides in different molar ratios at each addition step.

Template molecules typically contain fixed 5' and 3' terminal sequences which flank an internal region of 30-50 random nucleotides. A standard (1 μmole) scale synthesis will yield $10^{15}$-$10^{16}$ individual template molecules, sufficient for most SELEX experiments. The RNA library is generated from this starting library by in vitro transcription using recombinant T7 RNA polymerase. This library is then mixed with the target under conditions favorable for binding and subjected to stepwise iterations of binding, partitioning and amplification, using the same general selection scheme, to achieve virtually any desired criterion of binding affinity and selectivity. More specifically, starting from a mixture of nucleic acids, preferably comprising a segment of randomized sequence, the SELEX™ method includes steps of contacting the mixture with the target under conditions favorable for binding, partitioning unbound nucleic acids from those nucleic acids which have bound specifically to target molecules, dissociating the nucleic acid-target complexes, amplifying the nucleic acids dissociated from the nucleic acid-target complexes to yield a ligand-enriched mixture of nucleic acids, then reiterating the steps of binding, partitioning, dissociating and amplifying through as many cycles as desired to yield highly specific, high affinity nucleic acid ligands to the target molecule.

Within a nucleic acid mixture containing a large number of possible sequences and structures, there is a wide range of binding affinities for a given target. A nucleic acid mixture comprising, for example, a 20 nucleotide randomized segment can have $4^{20}$ candidate possibilities. Those which have the higher affinity constants for the target are most likely to bind to the target. After partitioning, dissociation and amplification, a second nucleic acid mixture is generated, enriched for the higher binding affinity candidates. Additional rounds of selection progressively favor the best ligands until the resulting nucleic acid mixture is predominantly composed of only one or a few sequences. These can then be cloned, sequenced and individually tested for binding affinity as pure ligands.

Cycles of selection and amplification are repeated until a desired goal is achieved. In the most general case, selection/amplification is continued until no significant improvement in binding strength is achieved on repetition of the cycle. The method may be used to sample as many as about $10^{18}$ different nucleic acid species. The nucleic acids of the test mixture preferably include a randomized sequence portion as well as conserved sequences necessary for efficient amplification. Nucleic acid sequence variants can be produced in a number of ways including synthesis of randomized nucleic acid sequences and size selection from randomly cleaved cellular nucleic acids. The variable sequence portion may contain fully or partially random sequence; it may also contain subportions of conserved sequence incorporated with randomized sequence. Sequence variation in test nucleic acids can be introduced or increased by mutagenesis before or during the selection/amplification iterations.

In one embodiment of SELEX™, the selection process is so efficient at isolating those nucleic acid ligands that bind most strongly to the selected target, that only one cycle of selection and amplification is required. Such an efficient selection may occur, for example, in a chromatographic-type process wherein the ability of nucleic acids to associate with targets bound on a column operates in such a manner that the column is sufficiently able to allow separation and isolation of the highest affinity nucleic acid ligands.

In many cases, it is not necessarily desirable to perform the iterative steps of SELEX™ until a single nucleic acid ligand is identified. The target-specific nucleic acid ligand solution may include a family of nucleic acid structures or motifs that have a number of conserved sequences and a number of sequences which can be substituted or added without significantly affecting the affinity of the nucleic acid ligands to the target. By terminating the SELEX™ process prior to completion, it is possible to determine the sequence of a number of members of the nucleic acid ligand solution family.

A variety of nucleic acid primary, secondary and tertiary structures are known to exist. The structures or motifs that have been shown most commonly to be involved in non-Watson-Crick type interactions are referred to as hairpin loops, symmetric and asymmetric bulges, pseudoknots and myriad combinations of the same. Almost all known cases of such motifs suggest that they can be formed in a nucleic acid sequence of no more than 30 nucleotides. For this reason, it is often preferred that SELEX procedures with contiguous randomized segments be initiated with nucleic acid sequences containing a randomized segment of between about 20-50 nucleotides.

The core SELEX™ method has been modified to achieve a number of specific objectives. For example, U.S. Pat. No. 5,707,796 describes the use of SELEX™ in conjunction with gel electrophoresis to select nucleic acid molecules with specific structural characteristics, such as bent DNA. U.S. Pat. No. 5,763,177 describes SELEX™ based methods for selecting nucleic acid ligands containing photoreactive groups capable of binding and/or photocrosslinking to and/or photo-inactivating a target molecule. U.S. Pat. No. 5,567,588 and U.S. application Ser. No. 08/792,075, filed Jan. 31, 1997, entitled "Flow Cell SELEX", describe SELEX™ based methods which achieve highly efficient partitioning between oligonucleotides having high and low affinity for a target molecule. U.S. Pat. No. 5,496,938 describes methods for obtaining improved nucleic acid ligands after the SELEX™ process has been performed. U.S. Pat. No. 5,705,337 describes methods for covalently linking a ligand to its target.

SELEX™ can also be used to obtain nucleic acid ligands that bind to more than one site on the target molecule, and to obtain nucleic acid ligands that include non-nucleic acid species that bind to specific sites on the target. SELEX™ provides means for isolating and identifying nucleic acid ligands which bind to any envisionable target, including large and small biomolecules including proteins (including both nucleic acid-binding proteins and proteins not known to bind nucleic acids as part of their biological function) cofactors and other small molecules. For example, U.S. Pat. No. 5,580,737 discloses nucleic acid sequences identified through SELEX™ which are capable of binding with high affinity to caffeine and the closely related analog, theophylline.

One potential problem encountered in the use of nucleic acids as therapeutics and vaccines is that oligonucleotides in the phosphodiester form may be quickly degraded in body fluids by intracellular and extracellular enzymes such as endonucleases and exonucleases before the desired effect is manifest. The SELEX method thus encompasses the identification of high-affinity nucleic acid ligands containing modified nucleotides conferring improved characteristics on the ligand, such as improved in vivo stability or improved delivery characteristics. Examples of such modifications include chemical substitutions at the ribose and/or phosphate and/or base positions. SELEX-identified nucleic acid ligands containing modified nucleotides are described, e.g., in U.S. Pat. No. 5,660,985, which describes oligonucleotides containing nucleotide derivatives chemically modified at the 5' and 2' positions of pyrimidines. U.S. Pat. No. 5,756,703 describes oligonucleotides containing various 2'-modified pyrimidines. U.S. Pat. No. 5,580,737 describes highly specific nucleic acid ligands containing one or more nucleotides modified with 2'-amino (2'-NH2), 2'-fluoro (2'-F), and/or 2'-O-methyl (2'-OMe) substituents.

Modifications of the nucleic acid ligands contemplated in this invention include, but are not limited to, those which provide other chemical groups that incorporate additional charge, polarizability, hydrophobicity, hydrogen bonding, electrostatic interaction, and fluxionality to the nucleic acid ligand bases or to the nucleic acid ligand as a whole. Modifications can also include 3' and 5' modifications such as capping. The modifications are known to one of ordinary skill in the art. Such modifications may be made post-SELEX process (modification of previously identified unmodified ligands) or by incorporation into the SELEX process.

The SELEX method encompasses combining selected oligonucleotides with other selected oligonucleotides and non-oligonucleotide functional units as described in U.S. Pat. No. 5,637,459 and U.S. Pat. No. 5,683,867. The SELEX method further encompasses combining selected nucleic acid ligands with lipophilic or non-immunogenic high molecular weight compounds in a diagnostic or therapeutic complex, as described in U.S. Pat. No. 6,011,020.

The identification of nucleic acid ligands to small, flexible peptides via the SELEX method has also been explored. Small peptides have flexible structures and usually exist in solution in an equilibrium of multiple conformers, and thus it was initially thought that binding affinities may be limited by the conformational entropy lost upon binding a flexible peptide. However, the feasibility of identifying nucleic acid ligands to small peptides in solution was demonstrated in U.S. Pat. No. 5,648,214. In this patent, high affinity RNA nucleic acid ligands to substance P, an 11 amino acid peptide, were identified.

Nucleic acid aptamer molecules are generally selected in a 5 to 20 cycle procedure. In one embodiment, heterogeneity is introduced only in the initial selection stages and does not occur throughout the replicating process.

The present invention describes the selection of aptamers capable of targeting alpha-toxin and method of using these aptamers to neutralize or inhibit the lethal effects of *Staphylococcus aureus* alpha-toxin for treatment of *S. aureus* infections. Alpha-toxin, also known as alpha-hemolysin (Hla), is the major cytotoxic agent released by bacterium *Staphylococcus aureus*. It is also the first identified member of the pore forming beta-barrel toxin family. This toxin consists mostly of beta-sheets (68%) with only about 10% alpha-helices. The hla gene on the *S. aureus* chromosome encodes the 293 residue protein monomer, which forms heptameric units on the cellular membrane to form a complete beta-barrel pore. This structure allows the toxin to perform its major function, development of pores in the cellular membrane, eventually causing cell death.

EXAMPLE 1

In Vitro Selection of *Staphylococcus aureus* Alpha-Toxin Aptamers

The DNA library for the selection process consisted of a 102 base single-stranded DNA (ssDNA) template containing a 42 nucleotide random region (N42) flanked by two constant regions for primer-binding sites: 5' ACC CCT GCA GGA TCC TTT GCT GGT ACC (SEQ ID NO: 1) NNNN (N=42) AGT ATC GCT AAT CAG TCT AGA GGG CCC CAG AAT (SEQ ID NO:2) 3'. The pool was then amplified via polymerase chain reaction (PCR) using 5' biotin labeled and 3' primers (Sigma-Genosys, The Woodlands, Tex. or INTE- GRATED DNA TECHNOLOGIES®, Coralville, Iowa) and finally used in the in vitro selection process.

Iterative rounds of selection and amplification of ssDNA aptamers were performed as described by Vivekananda and Kiel [19]. In brief, to exclude filter binding ssDNA sequences from the pool, the ssDNA was passed through a 0.45 μm HAWP filter (MF-MILLIPORE™, Bedford, Mass.) and washed with an equal volume of binding buffer containing 20 mM Tris-hydrochloric acid (HCL), pH 7.5, 45 mM sodium chloride (NaCl), 3 mM magnesium chloride, 1 mM EDTA, and 1 mM dithiothreitol (DTT). The collected pool of DNA was used in the SELEX™ process. In the present invention, ssDNA pools of 500 pmol for initial rounds and 200 pmol for later rounds were used in the selection process. ssDNA pools were denatured at 94° C. for 3 minutes, and then cooled immediately to 4° C. in binding buffer. Selection was performed by incubating ssDNA pools with an equimolar concentration of S. aureus α-toxin (LIST BIOLOGICALS, INC®, Campbell, Calif.) at room temperature for one hour in binding buffer with gentle rotation. After 1 hour, the aptamer-toxin complex was vacuum-filtered over a HAWP filter at 5 psi and washed three times with binding buffer. Single-stranded DNA retained on the filter was eluted by boiling with 7 M urea, 100 mM 4-morpholine-ethansulfonic acid (MES), pH 5.5 and 3 mM EDTA. Eluted ssDNA was then precipitated with an equal volume of isopropyl alcohol. The ssDNA was recovered by centrifugation at 4° C. and washed once with 70% ethanol. After a brief air dry, the DNA pellet was resuspended in sterile distilled water. Selected ssDNA sequences were amplified by PCR and used for the next round of selection. Negative selections were made by passing the DNA pool through the filters to remove non-specific binders.

The DNA pool from round 10 of the selection was amplified by PCR using cloning primers and the population was cloned using a TOPO TA Cloning Kit (INVITROGEN®, Carlesbad, Calif.) per manufacturer protocol. The cloned sequences were transformed into One SHOT® TOP10 chemically competent E. coli bacterial cells. Transformants with the aptamer inserts were selected using blue/white screening on LB plates containing ampicillin and 5-bromo-4-chloro-3-indolyl-b-D-galactopyranoside (X-gal). Approximately 50 colonies in total were picked randomly and PCR was performed to verify aptamer insert. The plasmid DNA from these clones was harvested and purified using a QIAprep Spin Miniprep Kit (QIAGEN®, Valencia, Calif.) then sequenced (INTEGRATED DNA TECHNOLOGIES®, Coralville, Iowa) for use in the in vitro neutralization study.

EXAMPLE 2

α-Toxin-Induced Jurkat T Cell Toxicity

Jurkat Clone E6-1 human T lymphocytes (ATCC #TIB-152, Manassas, Va.) were selected to study the effects of α-toxin. Cells were cultured in RPMI-1640 medium supplemented with 10% fetal bovine serum (FBS, Atlanta Biologicals, Lawrenceville, Ga.) and 1% Penicillin/streptomycin (Gibco BRL). α-toxin (LIST BIOLOGICALS, INC®, Campbell, Calif.) was reconstituted in sterile double distilled water at 500 ng/μl and stored at −80° C. Cells were maintained in a humidified incubator with 5% $CO_2$ and 95% air at 37° C. For cytotoxicity studies, Jurkat T cells were seeded at a density of $1 \times 10^5$ to $2 \times 10^6$ cells/ml in 24-well tissue culture plates. To determine the 50% lethal dose (LD50), either media alone or media with α-toxin was added to the cells at varying doses ranging from 50 to 100 ng/ml. All cells were incubated in a humidified incubator. To assess cell viability, the XTT Cell Proliferation Kit II (Roche Applied Science, Indianapolis, Ind.) protocol was performed 6 and 24 hours post challenge as per manufacturer's instructions. Percent viability was calculated as follows: [(A450 of toxin treated cells−A450 background)/A450 of untreated cells−A450 background)]×100. The 50% cytotoxicity is the amount of toxin necessary to kill 50% of cells. Multiple experiments were combined and the average±standard error of mean was graphed.

Figure 1:
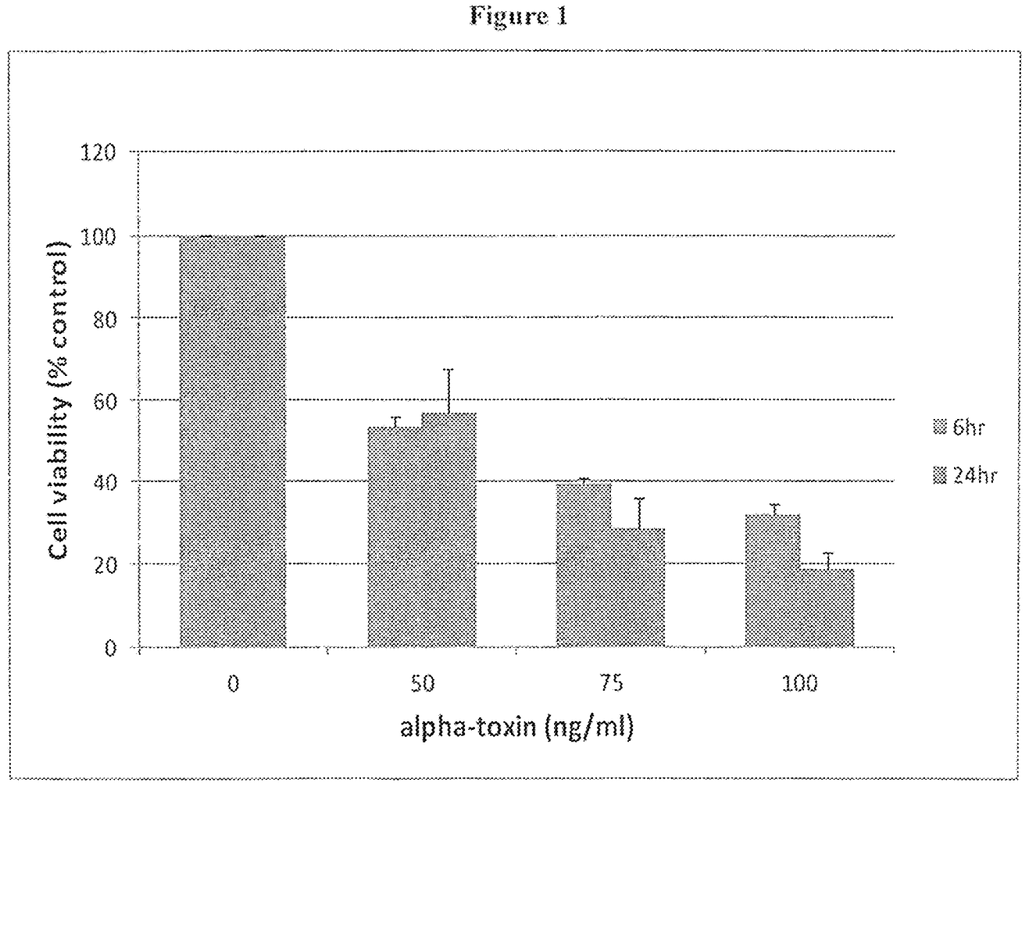
FIG. 1. Dose and time dependent toxicity induced by α-toxin in Jurkat T cells. Human Jurkat T cells were challenged with 50, 75 or 100 ng/ml of α-toxin in 24 well tissue culture plates. Cell viability was assessed 6 and 24 hours post challenge using an XTT cell proliferation assay. Control cells received media alone. The graph depicts percent cell viability compared to untreated control. Data are mean+SEM, n=4.

Result: Susceptibility of Jurkat T Cells to α-Toxin

α-toxin is toxic to various cell lines with varying degrees of sensitivity [1]. Six cell lines were tested for α-toxin sensitivity and data showed that RAW 264.7 and J774A.1 cells were insensitive to α-toxin. Among the other cell lines investigated, lung epithelial cell lines A549, H441 and Chinese hamster ovary (CHO) cells were sensitive to α-toxin at higher doses ranging from 0.5-3 μg/ml for induction of cytolysis (data not shown). In agreement with other studies [20], human Jurkat T cells were highly susceptible to α-toxin and the dose required to achieve 45-50% killing was 50 ng/ml at 6 hours post exposure. Based on this data, we selected human Jurkat T cells to assay in vitro toxic effects of α-toxin. To examine the effects of increasing doses of α-toxin on cell viability, Jurkat T cells were treated with 50, 75 and 100 ng/ml of α-toxin in 24 well plates. The percentage of viable toxin treated cells versus untreated control cells was determined at 6 and 24 h post challenge using an XTT cell proliferation assay by measuring the optical density at 450 nm. As shown in FIG. 1, increasing concentration of α-toxin resulted in low cell survival rate over the time course. α-toxin at 50 ng/ml resulted about 55 to 58% cell survival following 6 and 24 hours exposure (FIG. 1). At 75 μg/ml toxin dose, cell viability dropped to 40% and 30% at 6 and 24 hours post challenge, respectively. As expected, the highest dose of α-toxin, 100 ng/ml, induced profound toxicity by killing almost 70% and 82% at 6 and 24 hours post challenge, respectively.

EXAMPLE 3

α-Toxin Neutralization Assay

To analyze the neutralization activity of the selected aptamers against the cytotoxic effects of S. aureus α-toxin, 24-well tissue culture plates were seeded as described above with Jurkat T cells. The final concentration of α-toxin used for the experiments was selected to achieve 50% killing of Jurkat T cells (final concentration of 50 ng/ml). For treatments, either reconstituted α-toxin (50 ng/ml) alone or α-toxin plus phosphorothioate-modified aptamer at 500 and 1000× molar excess of α-toxin was added to the cells. These two aptamer concentrations were chosen to be tested in the neutralization studies based on earlier experience with other bacterial toxins and the respective aptamers. Cell culture plates were incubated with the additives at 37° C. in a humidified incubator. At 6 hours post challenge, cell viability was assessed using an XTT Cell Proliferation Kit II assay following the manufacturer's instructions. Untreated cells served as the control. Percent cell viability was calculated as described above.

Results: Neutralization of α-Toxin Cytotoxicity by Specific Aptamers

Figure 2:
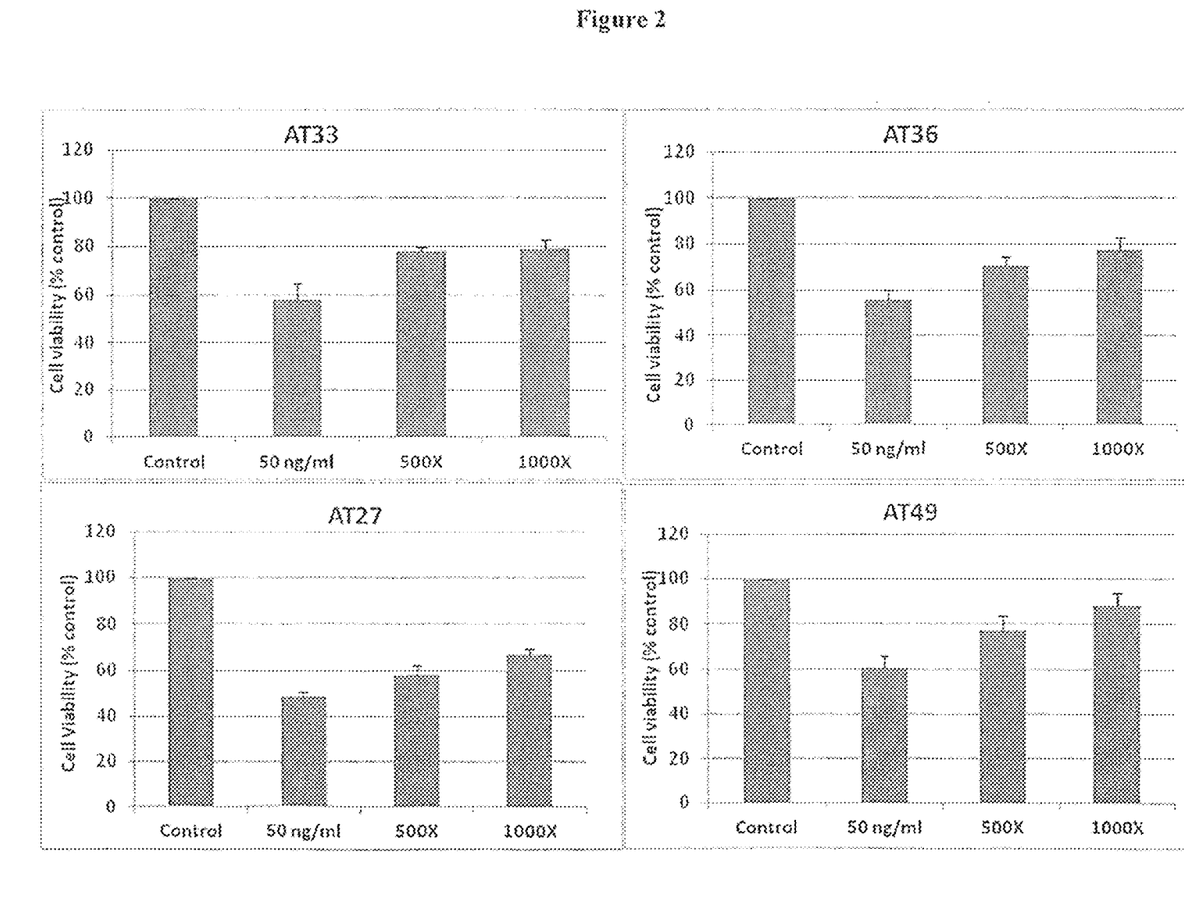
FIG. 2. Neutralization of α-toxin induced cytotoxicity by toxin specific aptamers in a Jurkat T cell cytotoxicity assay. Cells were treated with either 50 ng/ml of α-toxin or α-toxin plus individual aptamers (AT-27, AT-33, AT-36, or AT-49) at 500 or 1000× molar excess of α-toxin protein. The mixture was then added to the cells and transferred to a humidified incubator. Cell viability was assessed 6 hours post challenge by XTT cell proliferation assay. Cells grown in parallel but not treated with α-toxin were used to define 100% viability (Control). Data are mean+SEM, n=3. *$p \leq 0.05$ as determined by ANOVA followed by Turkey HSD test.
Figure 3:
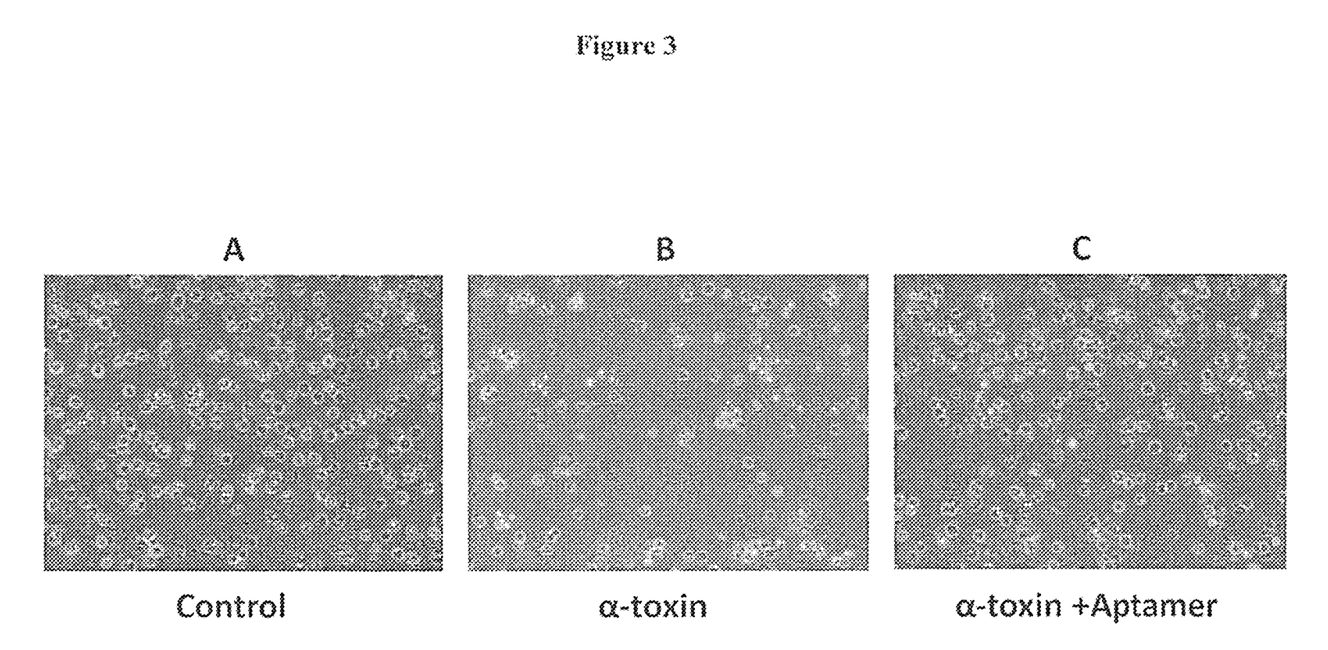
FIG. 3. Digital pictures of Jurkat T cells exhibiting aptamer mediated cytoprotection. Cells were challenged as follows at 37° C.: (A) media alone as control, (B) α-toxin (100 ng/ml), (C) α-toxin (100 ng/ml) plus AT-33 aptamer (500× the molar concentration of α-toxin). Digital pictures were taken 24 hours post challenge (20× lens).

After 10 rounds of SELEX, 49 potential anti-α-toxin aptamers were selected randomly. All 49 aptamers were tested for their ability to neutralize α-toxin cytotoxicity in vitro. To evaluate whether the α-toxin aptamers were able to reduce or eliminate cytotoxicity of α-toxin, a Jurkat T cell based assay was utilized. The toxic dose that killed about 50-60% of cells (LD50) in 6 hours was determined to be 50 ng/ml (FIG. 1). Thus, for the following studies a concentration of 50 ng/ml of α-toxin was used for α-toxin aptamer screening. Among the 49 aptamers tested, four aptamers, AT-27 (SEQ ID NO: 9), AT-33 (SEQ ID NO:10), AT-36 (SEQ ID NO:11) and AT-49 (SEQ ID NO:12) had a neutralizing effect on α-toxin toxicity and inhibited cytolysis of Jurkat T cells. Aptamer doses of 500 and 1000× molar excess of α-toxin and an exposure time of 6 hours were chosen based on earlier studies with other bacterial toxins and their respective aptamers (data not shown). The above mentioned four aptamers overall reduced cell mortality caused by α-toxin, and cell viability was increased up to almost 85% of the controls. AT-33 increased viability to about 80%, even at the 500× concentration (FIG. 2). AT-36 aptamer produced similar results at the 1000× aptamer concentration. Remarkably, AT-49 gave the highest protection by increasing viability to almost 85-90% of control cells. Comparatively, AT-27 exhibited limited neutralization by increasing viability to about 60 to 65% of controls. It should be further noted that these effects of the α-toxin aptamers are statistically significant with a $p \leq 0.05$ as determined by ANOVA followed by Turkey HSD test (FIG. 2). Thus, aptamers at the indicated doses are required to block the cytotoxic actions of α-toxin. Digital pictures of Jurkat T cells exhibiting aptamer mediated cytoprotection presented in FIG. 3, is further evidence for the neutralization effect of AT-33 aptamer against α-toxin.

EXAMPLE 4

Aptamers AT-36 and AT-33 Inhibit α-Toxin Induced TNF-Alpha and IL-17 Gene Transcription During infection, cytokines are known to be involved in the modulation of biological functions including cell death. S. aureus α-toxin and other pore forming toxins have been identified to trigger the upregulation of proinflammatory cytokines such as TNF-α, Il-1β and IL-8 [21-23]. Liang et al. further confirmed that TNF-α specific antibodies inhibited the toxicity of α-toxin in human lung epithelial cell line[21]. Recent findings also suggested that S. aureus α-toxin induced the expression and synthesis of IL-17 in peripheral blood mononuclear cells, indicating its possible role in the toxic effects of α-toxin [24]. To better understand the response of Jurkat T cells to α-toxin, the expression of the inflammatory cytokines TNF-α and IL-17 were analyzed at the mRNA level. To examine the effect of α-toxin on TNF-α and IL-17 gene expression, Jurkat T cells were stimulated with 50 ng/ml α-toxin for 6 hours. Initial experiments showed that IL-17 gene expression was undetected at 50 ng/ml α-toxin (data not shown). In subsequent experiments of IL-17 expression, the α-toxin dose was increased to 100 ng/ml and cells were stimulated for 24 hours.

For TNF-α expression, Jurkat T cells were seeded in tissue culture dishes and challenged with either 50 ng/ml α-toxin alone or toxin in combination with AT-36 aptamer at 500 or 1000× molar excess of α-toxin for 6 hours. At the end of the treatment, cells were harvested and frozen immediately at −80° C. until further use. For IL-17 expression, cells were treated with 100 ng/ml α-toxin alone or toxin in combination with AT-33 (SEQ ID NO:10) or AT-36 (SEQ ID NO:11) aptamers at 500× molar excess of α-toxin. Cells were harvested 24 hours post challenge and stored at −80° C. Control cells received media only.

Total RNA was isolated using Tri Reagent (AMBION®, Austin, Tex.) per the manufacturer's protocol. Quantity and purity of RNA preparations were determined by measuring the absorbance at 260 and 280 nm. Fixed amounts of total cellular RNA were reverse-transcribed into cDNA using the SuperScript III One-Step RT-PCR System with Platinum Taq (INVITROGEN®, Carlesbad, Calif.). The house keeping gene GAPDH was used as an internal control to normalize the PCR signal for the amount of RNA added to the reverse transcription reactions, and the target gene expression was normalized to the untreated control. Data are expressed as fold change of the gene expression. The amplification of cDNA by PCR was performed using the following primers: TNF-α forward 5' GAGTGACAAGCCTGTAGCCCATGT-TGTAGCA 3'(SEQ ID NO:3), reverse 3'GCAATGATC-CCAAAGTAGACCTGCCCAGACT 5'(SEQ ID NO:4), IL-17 forward 5' CCACGAAATCCAGGATGCCCAAAT 3'(SEQ ID NO: 5), reverse 5' ATTCCAAGGTGAGGTG-GATCGGTT 3'(SEQ ID NO:6), and GAPDH forward 5' GTCGGTGTGAACGGATTT 3'(SEQ ID NO:7), reverse 5' ACTCCACGACGTACTCAGC 3'(SEQ ID NO:8). PCR amplification was done with the following specification: TNF-α, 35 cycles of the following scheme: 2 min at 94° C. initial denaturation, 15 sec at 94° C., 30 sec at 66° C., 1 min at 68° C. followed by 5 min of primer extension at 68° C.; IL-17, 40 PCR cycles were performed with the following conditions: 2 min at 94° C. denaturation, 15 sec at 94° C., 30 sec at 55° C., 1 min at 72° C. followed by 5 min of primer extension at 68° C.; GAPDH: 30 cycles were performed with the following PCR specification: 2 min at 94° C. initial incubation, 15 sec at 94° C., 30 sec at 50° C., 1 min at 68° C. followed by 5 min of primer extension at 68° C. The amplified products were subjected to electrophoresis in a 2% agarose gel containing ethidium bromide and visualized by UV transillumination. Gels were imaged and gene expression levels in treated samples were standardized to expression levels in controls using an AlphaImager HP System (Protein Simple). The gene expression levels in the controls was set to 1.0.

Figure 4:
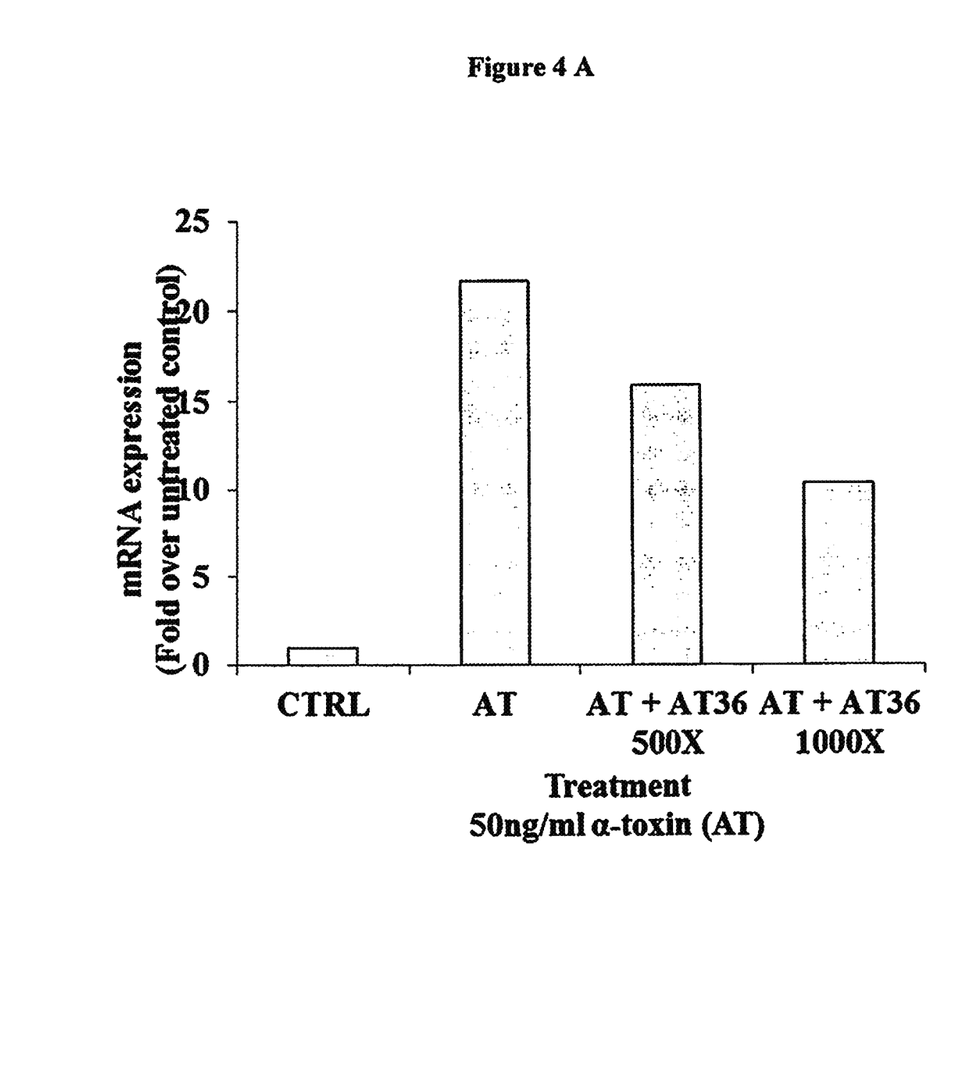
Figure 5:
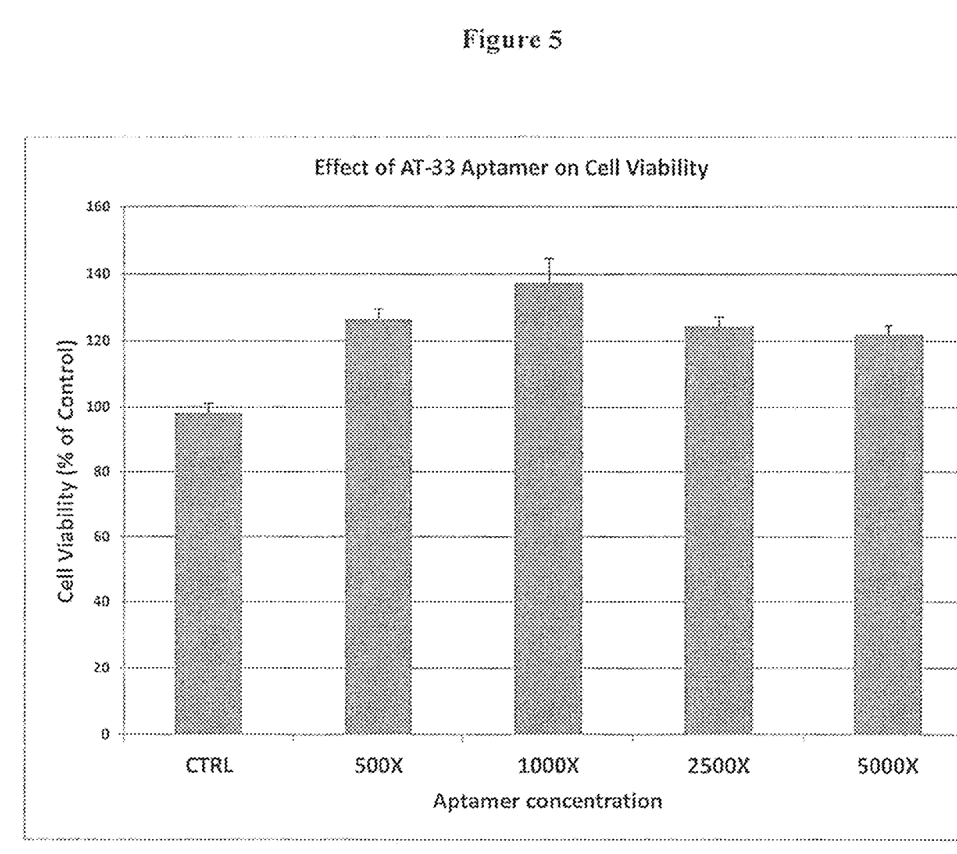
FIG. 5. Non-toxic effect of α-toxin specific aptamers on Jurkat T cells. Cells were treated with AT-33 aptamer at 500, 1000, 2500 and 5000× molar excess of α-toxin concentration (50 ng/ml) and incubated for 24 hours. Cell viability was assessed using an XTT cell proliferation kit. Cells treated with media without aptamer served as the control. Data presented are mean+SEM, n=3.

Results: Aptamers AT-36 and AT-33 Inhibit α-Toxin Induced TNF-Alpha and IL-17 Gene Transcription At the designated times, cells were collected and TNF-α and IL-17 gene transcription was assessed by RT-PCR. As indicated in FIG. 4, untreated controls exhibited basal levels of TNF-α (FIG. 4. A) and IL-17 (FIG. 4. B), whereas TNF-α and IL-17 gene transcription was induced by α-toxin. However, co-treatment with AT-36 aptamer decreased the TNF-α mRNA levels in a dose dependent manner. TNF-α message levels were elevated more than 20-fold compared to media treated controls. Interestingly, TNF-α mRNA levels were reduced to 5- and 10-fold in cells treated with 500 and 100× molar concentration of AT36 aptamer, respectively. It is worthy to note that this transcriptional suppression by the aptamer is dose dependent (FIG. 4A). Data confirmed that exposure to α-toxin increases IL-17 expression in Jurkat T cells, as previously reported [24]. As shown in FIG. 4, untreated cells sustained basal IL-17 mRNA levels. However, exposure to α-toxin increased IL-17 mRNA levels to almost 3.25-fold compared to the untreated controls. Co-treatment with aptamers AT-33 and AT-36 at 500× suppressed IL-17 gene transcription levels down to basal level observed in untreated control cells (FIG. 4). Taken together, the presented data indicate that AT-33 and AT-36 aptamers inhibited upregulation of α-toxin stimulated TNF-α and IL-17 gene transcription in Jurkat T cells.

The current application shows the successful identification of four DNA aptamers, AT-27, AT-33, AT-36 and AT-49 against S. aureus α-toxin/hemolysin. To the best of our knowledge, this is the first time α-toxin targeted aptamers with the capacity to inhibit cell death have been reported.

Aptamers in the present study were selected by SELEX iterative process using highly pure α-toxin. The selected aptamers of this invention are able to inhibit cytolytic and cytotoxic effects with high-specificity in an in vitro model. The toxic effects of α-toxin vary depending on target cells and also the toxin concentration. For example, in Jurkat T cells, 50 ng/ml is required to obtain LD50, whereas in lung epithelial cells A549 and H441 cells, toxin sensitivity is achieved at microgram concentrations. This is in agreement with published work indicating that at lower concentrations, α-toxin induced apoptosis in Jurkat cells. Higher doses caused necrosis signifying that the modes of cell death may depend on the dose of the toxin[5, 32]. The application further shows that α-toxin is capable of inducing the transcription of TNF-α and IL-17 genes in Jurkat T cells. As anticipated, aptamers AT-33 and AT-36 inhibited the transcriptional activation of these inflammatory cytokine genes.

The current application also teach a therapeutic composition having binding affinity to Staphylococcus aureus alpha-toxin, which comprise one or more aptamers selected from the group consisting of AT-22 (SEQ ID NO:9), AT-33 (SEQ ID NO: 10), AT-36 (SEQ ID NO: 11), and AT-49 (SEQ ID NO:12) in a pharmaceutical acceptable form. An acceptable pharmaceutical acceptable form may include, but not limited to, powders, gels, creams, ointments, suppositories, films, tablets, capsules, caplets, implants, emulsions, aerosols and sprays. Binding of a therapeutic effective amount of the inventive aptamer to the alpha-toxin neutralizes the alpha-toxin and possibly result in decreased binding and/or pore-forming ability of the toxin against the cells. The therapeutic composition may comprise a pharmaceutical acceptable carrier, such as water, aluminum hydroxide etc.

The instant application also describes a method for neutralizing Staphylococcus aureus alpha-toxin in a subject. Patients suspected or confirmed of a Staphylococcus aureus infection are identified, and then administered a therapeutically effective amount of a pharmaceutical composition comprising aptamers that neutralizes alpha-toxin. The atamers in this pharmaceutical composition may inhibits transcriptional activation of inflammatory cytokine genes and reduce the virulence of the Staphylococcus aureus. In one embodiment, the aptamer inhibits transcriptional activation of TNF-α and IL-17 genes.

The instant application also discloses a method for detecting Staphylococcus aureus alpha-toxin in a sample. The method comprising: tagging one or more of inventive aptamers (AT-22 (SEQ ID NO:9), AT-33 (SEQ ID NO: 10), AT-36 (SEQ ID NO: 11), and AT-49 (SEQ ID NO:12)) with a reporting molecule; contacting a sample suspected of containing Staphylococcus aureus alpha-toxin with said tagged aptamer; wherein a change in the signal from the aptamer-reporting molecule complex indicate the presence of Staphylococcus aureus alpha-toxin.

REFERENCES

1. Bhakdi S, Tranum-Jensen J (1991) Alpha-toxin of Staphylococcus aureus. Microbiol Rev 55: 733-751.
2. Lowy FD, Staphylococcus aureus infections. (1998) N Engl J Med. 339: 520-532.
3. Foster TJ. Staphylococcus aureus "super bug". J Clin Invest 114: 1693-1696.
4. Zetola N, Francis J S, Nuermberger E L, Bishai W R Community acquired methicillin-resistant Staphylococcus aureus: an emerging threat (2005) Lancet Infect Dis 5:275-286.
5. Bantel H, Sinha B, Domschke W, Peters G, Schulze-Osthoff K, et al (2001) Alpha-toxin is a mediator of Staphylococcus aureus-induced cell death and activates caspases via the intrinsic pathway independent of death receptor signaling. J Cell Biol 155: 637-648.
6. Gouaux J E, Braha O, Hobaugh M R, Song L, Cheley S, et al (1994) Subunit stoichiometry of staphylococcal alpha-hemolysin in crystals on membranes: A heptameric transmembrane pore. (1994) Proc Natl Acad Sci USA 91: 12828-12831.
7. Valeva A, Weisser A, Walker B, Kehoe M, Bayley H, et al (1996) Molecular architecture of a toxin pore: a 15-residue sequence lines the transmembrane channel of staphylococcal α-toxin. EMBO J 15: 1857-1864.
8. Kennedy A D, Wardenburg J B, Gardner D J, Long D, Whitney A R, et al (2010) Targeting of alpha-hemolysin by active or passive immunization decreases severity of USA300 skin infection in a mouse model. J Infect Dis 202: 1050-1058.
9. Wardenburg J B, Patel R J, Schneewind R J O (2007) Surface proteins and exotoxins are required for the pathogenesis of Staphylococcus aureus pneumonia. Infect Immun 75: 1040-1044.
10. Callegan M C, Engel L S, Hill J M, O'Callaghan R J (1994) Corneal virulence of Staphylococcus aureus: roles of alpha-toxin and protein A in pathogenesis. Infect Immun 62: 2478-2482.
11. Menzies B E, Kemodle D S (1996) Passive immunization with antiserum to a nontoxic alpha-toxin mutant from Staphylococcus aureus is protective in a murine model. Infect Immun 64: 1839-1841.
12. Ragle B E, Wardenburg J B (2009) Anti-alpha-hemolysin monoclonal antibodies mediate protection against Staphylococcus aureus pneumonia. Infect Immun 77: 2712-2718.
13. Tuerk C, Gold L (1990) Systematic evolution of ligands by exponential enrichment: RNA ligands to bacteriophage T4 DNA polymerase. Science. 249: 505-510.
14. Ellington A D, Szostak J W (1990) In vitro selection of RNA molecules that bind specific ligands Nature 346: 818-822.
15. Nimjee S M, Rusconi C P, Sullenger B A (2005) Aptamers: an emerging class of therapeutics. Annu Rev Med 56: 555-583.
16. Klussmann S (Ed.) (2006) The Aptamer Hand Book: Functional oligonucleotides and their application. Wiley-VCH Verlag GmbH & Co, Germany.
17. Bouchard P R, Hutabarat R M, Thompson K M (2010) Discovery and development of therapeutic aptamers. Annu Rev Pharmacol Toxicol 50: 237-257.
18. Keefe A D, Pai S, Ellington A D Aptamers as therapeutics (2010) Nature Rev Drug Discov 9: 537-550.
19. Vivekananda J, Kiel J L (2006) Anti-Francisella tularensis DNA aptamers detect tularemia antigen from different subspecies by aptamer-linked immobilized sorbent assay. Lab Invest 86: 610-618.
20. Haslinger B, Strangfeld K, Peters G, Schulze-Osthoff K, Sinha B (2003) Staphylococcus aureus alpha-toxin induces apoptosis in peripheral blood mononuclear cells: role of endogenous tumor necrosis factor-alpha and the mitochondrial death pathway. Cell Microbiol 10: 729-741.
21. Liang X, Ji Y (2007) Involvement of α5β1-integrin and TNF-α in Staphylococcus aureus α-toxin-induced death of epithelial cells. Cell Microbiol 9: 1809-1821.
22. Bhakdi S, Muhly M, Korom S, Hugo F (1989) Release of interleukin-1 beta associated with potent cytocidal action of staphylococcal alpha-toxin on human monocytes. Infect Immun 57 (1989) 3512-3519.

23. Dragneva Y, Anuradha C D, Valeva A, Hoffmann A, Bhakdi S, et al. (2001) Subcytocidal attack by staphylococcal alpha-toxin activates NF-kappaB and induces interleukin-8 production. Infect. Immun 69: 2630-2635.
24. Niebuhr M, Gathmann M, Scharonow H, Mamerow D, Mommert S, et al. (2011) Staphylococcal Alpha-Toxin Is a Strong Inducer of Interleukin-17 in Humans. Infect Immun 79: 1615-1622.
25. Sundaram P, Kurniawan H, Byrne M E, Wower J (2013) Therapeutic RNA aptamers in clinical trials. Eur J Pharm Sci 48: 259-271.
26. Ni X, Castanares M A, Mukherjee A, Lupold S E (2011) Nucleic acid aptamers: clinical applications and promising new horizons. Curr Med Chem 18: 4206-4214.
27. T. W. Chang, M. Blank, P. Janardhanan, Singh B R, Mello C, et al. (2010) In vitro selection of RNA aptamers that inhibit the activity of type A botulinum neurotoxin. Biochem Biophys Res Commun. 396: 854-860.
28. Wen A Q, Yang Q W, Li J C, Lv F L, Zhong Q et al. (2009) A novel lipopolysaccharide-antagonizing aptamer protects mice against endotoxemia. Biochem Biophys Res Commun. 382: 140-144.
29. S. Fan, F. Wu, F. Martiniuk, Hale M L, Ellington A E, et al. (2008) Protective effects of anti-ricin A-chain RNA aptamer against ricin toxicity. World J Gastroenterol 14: 6360-6365.
30. Liang H R, Liu Q, Zheng X X, Gai W W, Xue X H, et al. (2013) Aptamers targeting rabies virus-infected cells inhibit viral replication both in vitro and in vivo. Virus Res 173: 398-403.
31. DeGrasse J A (2012) A single-stranded DNA aptamer that selectively binds to *Staphylococcus aureus* enterotoxin B. PLoS One 7 (3) e33410.
32. Essmann F, Bantel H, Totzke G, Engels I H, Schulze-Osthoff K, et al. (2003) *Staphylococcus aureus* alpha-toxin-induced cell death: predominant necrosis despite apoptotic caspase activation. Cell Death Differ. 10: 1260-1272
33. Stoltenburg, R, Reinemann, C., Strehlitz B., (2007) SELEX—A (r)evolutionary method to generate high-affinity nucleic acid ligands. Biomolecular Engineering, 24:381-403.

What is claimed is:

1. An aptamer that binds to *Staphylococcus aureus* alpha toxin and reduces its cytolytic and cytotoxic effects, wherein the aptamer comprises a nucleotide sequence selected from the group consisting of SEQ ID NO: 9, SEQ ID NO: 10, SEQ ID NO: 11, and SEQ ID NO: 12.

2. A therapeutic composition comprising the aptamer of claim 1 in a pharmaceutically acceptable form.

3. A method of diagnosing *Staphylococcus aureus* infection in a sample comprising:
   a) providing a sample from a subject suspected of *Staphylococcus aureus* infection; and
   b) contacting the sample with an aptamer having a sequence selected from the group consisting of SEQ ID NO:9 SEQ ID NO: 10, SEQ ID NO: 11, and SEQ ID NO:12, said aptamer complexed with a reporter moiety, wherein a signal is generated upon binding to a *Staphylococcus aureus* alpha-toxin.

4. A method for inhibiting cytolytic and cytotoxic effects of *Staphylococcus aureus* alpha toxin in a subject comprising:
   a) administering to the subject a therapeutically effective amount of a composition comprising an aptamer that binds to *Staphylococcus aureus* alpha toxin, wherein the aptamer has a sequence selected from the group consisting of SEQ ID NO: 9, SEQ ID NO: 10, SEQ ID NO: 11, and SEQ ID NO: 12.

5. The method of claim 4, wherein the aptamer inhibits transcriptional activation of TNF-α and IL-17 genes.

* * * * *

SEQUENCE LISTING

<160> NUMBER OF SEQ ID NOS: 12

<210> SEQ ID NO 1
<211> LENGTH: 27
<212> TYPE: DNA
<213> ORGANISM: Artificial Sequence
<220> FEATURE:
<223> OTHER INFORMATION: the 5' region of DNA template N42

<400> SEQUENCE: 1
acccctgcag gatcctttgc tggtacc                                          27

<210> SEQ ID NO 2
<211> LENGTH: 33
<212> TYPE: DNA
<213> ORGANISM: Artificial Sequence
<220> FEATURE:
<223> OTHER INFORMATION: 3' region of template N42

<400> SEQUENCE: 2
agtatcgcta atcagtctag agggcccag aat                                    33

<210> SEQ ID NO 3
<211> LENGTH: 31
<212> TYPE: DNA
<213> ORGANISM: Artificial Sequence
<220> FEATURE:
<223> OTHER INFORMATION: TNF-alpha forward primer

<400> SEQUENCE: 3
gagtgacaag cctgtagccc atgttgtagc a                                     31

<210> SEQ ID NO 4
<211> LENGTH: 31
<212> TYPE: DNA
<213> ORGANISM: Artificial Sequence
<220> FEATURE:
<223> OTHER INFORMATION: TNF-alpha reverse primer

<400> SEQUENCE: 4
gcaatgatcc caaagtagac ctgcccagac t                                     31

```
<210> SEQ ID NO 5
<211> LENGTH: 24
<212> TYPE: DNA
<213> ORGANISM: Artificial Sequence
<220> FEATURE:
<223> OTHER INFORMATION: IL-17 forward primer

<400> SEQUENCE: 5
ccacgaaatc caggatgccc aaat                                          24

<210> SEQ ID NO 6
<211> LENGTH: 24
<212> TYPE: DNA
<213> ORGANISM: Artificial Sequence
<220> FEATURE:
<223> OTHER INFORMATION: IL-17 reverse primer

<400> SEQUENCE: 6
attccaaggt gaggtggatc ggtt                                          24

<210> SEQ ID NO 7
<211> LENGTH: 18
<212> TYPE: DNA
<213> ORGANISM: Artificial Sequence
<220> FEATURE:
<223> OTHER INFORMATION: GAPDH forward primer

<400> SEQUENCE: 7
gtcggtgtga acggattt                                                 18

<210> SEQ ID NO 8
<211> LENGTH: 19
<212> TYPE: DNA
<213> ORGANISM: Artificial Sequence
<220> FEATURE:
<223> OTHER INFORMATION: GAPDH reserve primer

<400> SEQUENCE: 8
actccacgac gtactcagc                                                19

<210> SEQ ID NO 9
<211> LENGTH: 42
<212> TYPE: DNA
<213> ORGANISM: Artificial Sequence
<220> FEATURE:
<223> OTHER INFORMATION: AT27

<400> SEQUENCE: 9
cctttactct ttgtttcttc tacttactat actattactt ag                      42

<210> SEQ ID NO 10
<211> LENGTH: 42
<212> TYPE: DNA
<213> ORGANISM: Artificial Sequence
<220> FEATURE:
<223> OTHER INFORMATION: AT33

<400> SEQUENCE: 10
tataacacac catcatttac tattccattc tataataact aa                      42

<210> SEQ ID NO 11
<211> LENGTH: 42
<212> TYPE: DNA
<213> ORGANISM: Artificial Sequence
<220> FEATURE:
<223> OTHER INFORMATION: AT36
```

```
<400> SEQUENCE: 11
taacccacat aataaacata taattcattc tttaacattc cc                    42

<210> SEQ ID NO 12
<211> LENGTH: 42
<212> TYPE: DNA
<213> ORGANISM: Artificial Sequence
<220> FEATURE:
<223> OTHER INFORMATION: AT47

<400> SEQUENCE: 12
tgaagtatat atttctaaca ccattcttcc tcctacactc ca                    42
```